United States Patent
Foley et al.

(10) Patent No.: US 10,071,941 B2
(45) Date of Patent: Sep. 11, 2018

(54) TERPENE-DERIVED COMPOUNDS AND METHODS FOR PREPARING AND USING SAME

(71) Applicant: P2 Science, Inc., Woodbridge, CT (US)

(72) Inventors: Patrick Foley, New Haven, CT (US); Yonghua Yang, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 15/317,642

(22) PCT Filed: Jun. 10, 2015

(86) PCT No.: PCT/US2015/035097
§ 371 (c)(1),
(2) Date: Dec. 9, 2016

(87) PCT Pub. No.: WO2015/191706
PCT Pub. Date: Dec. 17, 2015

(65) Prior Publication Data
US 2017/0113988 A1    Apr. 27, 2017

Related U.S. Application Data

(60) Provisional application No. 62/010,407, filed on Jun. 10, 2014.

(51) Int. Cl.
*C07C 29/00* (2006.01)
*C07C 33/00* (2006.01)
*C07C 29/147* (2006.01)

(52) U.S. Cl.
CPC .................................. *C07C 29/147* (2013.01)

(58) Field of Classification Search
CPC ............................ C07C 29/147; C07C 33/025
USPC ......................................................... 568/377
See application file for complete search history.

(56) References Cited

U.S. PATENT DOCUMENTS

| | | |
|---|---|---|
| 3,023,244 A | 2/1962 | Eschinasi |
| 3,699,169 A | 10/1972 | Bertele et al. |
| 5,756,821 A | 5/1998 | Dilk et al. |
| 6,395,695 B1 | 5/2002 | Sivik |
| 6,545,186 B2 | 4/2003 | Giselbrecht et al. |
| 2004/0186042 A1 | 9/2004 | Schmaus et al. |
| 2013/0338150 A1 | 12/2013 | Boehme et al. |
| 2016/0332952 A1 | 11/2016 | Foley et al. |

FOREIGN PATENT DOCUMENTS

| | | |
|---|---|---|
| EP | 0761629 A1 | 3/1997 |
| WO | WO 2009/061806 A2 | 5/2009 |
| WO | WO 2013/053102 A1 | 4/2013 |
| WO | WO 2015/106293 A1 | 7/2015 |
| WO | WO 2015/191706 A1 | 12/2015 |

OTHER PUBLICATIONS

Chen M. et al. "A Predictably Selective Aliphatic C—H Oxidation Reaction for Complex Molecule Synthesis", *Science*, vol. 318, 2007, pp. 783-787.
Cahn, R. S. et al. "Specification of Molecular Chirality" *Angew. Chem. Inter. Edit.* 1966, vol. 5, No. 4, p. 385-415.
Cahn, R. S. and Ingold, C. K. "Specification of Configuration About Quadricovalent Asymmetric Atoms" *J. Chem. Soc.* 1951 (London), p. 612-622.
Cahn, R. S. et al. "The Specification of Asymmetric Configuration in Organic Chemistry" *Experientia* 1956, vol. 12, p. 81-94.
Cahn, R. S. "An Introduction to the Sequence Rule. A System for the Specification of Absolute Configuration" *Journal of Chemical Education* 1964 (London), vol. 41, No. 3, p. 116-125.
Competition Science Vision Aug. 2000, *Pratiyogita Darpan*, vol. 3, No. 30, p. 799.
Gross, R. A., Jr. "Ozonolysis Problems That Promote Student Reasoning" *Journal of Chemical Education*, vol. 83, No. 4, 2006, p. 604-609.
PubChem-CID-107500001, Oct. 26, 2006, 17 pages.
Willand-Charnley, R. et al. "Pyridine is an Organocatalyst for the Reductive Ozonolysis of Alkenes" *Org Lett.* vol. 14, No. 9, May 2012, p. 2242-2245.

*Primary Examiner* — Sikarl A Witherspoon
(74) *Attorney, Agent, or Firm* — Hoxie & Associates LLC

(57) ABSTRACT

The invention relates to terpene-derived compounds, such as acids, esters thereof, produced by ozonolysis of terpenes, and to alcohols, amides, nitriles derived therefrom, as well as to processes for synthesizing them. Specifically, 2,3,7-trimethyloct-6-en-2-ol, 2,3,7-trimethyloct-7-en-2-ol, or a mixture thereof, produced by Grignard reaction of a terpene derived carboxylate with methyl magnesium bromide is disclosed.

19 Claims, 4 Drawing Sheets

TERPENE-DERIVED COMPOUNDS AND METHODS FOR PREPARING AND USING SAME

RELATED APPLICATIONS

This application is a U.S. National Phase application, filed under 35 U.S.C. § 371(c), of International Application No. PCT/US2015/035097, filed Jun. 10, 2015, which claims the benefit of and priority to U.S. Provisional Patent Application No. 62/010,407, filed Jun. 10, 2014, titled "TERPENE-DERIVED COMPOUNDS AND METHODS FOR PREPARING AND USING SAME," the entireties of each of which are incorporated by reference herein for all purposes.

BACKGROUND OF THE INVENTION

Ozonolysis of terpenes and analogs thereof can produce aldehydes that are used as ingredients in flavors and fragrances. See, e.g., U.S. Pat. Nos. 3,023,244, 3,699,169 and 6,545,186, and WO 2013/053102.

It is not uncommon that about 5-30% of the desired aldehydic product from the ozonolysis procedure is over-oxidized, producing the corresponding acid. The over-oxidized acid product is generally regarded as waste.

SUMMARY OF THE INVENTION

This invention relates to cost-efficient isolation of the acid product and application thereof in the industry of, e.g., flavors, fragrances, and preservatives.

In one aspect, the invention relates to a method of producing a compound of formula I or a salt thereof:

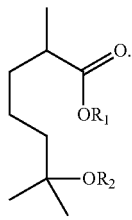
(I)

In this formula, $R_1$ is H, unsubstituted or substituted $C_1$-$C_{10}$ alkyl, or unsubstituted or substituted $C_2$-$C_{10}$ alkenyl, and $R_2$ is H, unsubstituted or substituted $C_1$-$C_{10}$ alkyl, or $COR_a$, in which $R_a$ is H or unsubstituted or substituted $C_1$-$C_{10}$ alkyl.

The method includes reacting a compound having the formula IB

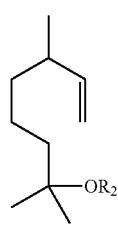
(IB)

with ozone and subsequently with an oxidant different from ozone to obtain the compound of formula (I) wherein $R_1$ is H.

Alternatively, the method includes (1) reacting a compound having the formula IB

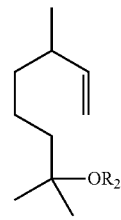
(IB)

with ozone and subsequently with a reductant to obtain a mixture comprising the compound of formula (I) wherein $R_1$ is H and a compound of formula (IC):

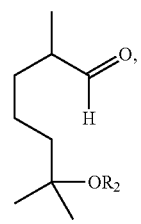
(IC)

and (2) separating the compound of formula (I) wherein $R_1$ is H from the compound of formula (IC).

In another aspect, the invention relates to a method of producing a compound of formula I or a salt thereof, the method including providing an aqueous mixture comprising the compound of formula (I) wherein $R_1$ is H and a compound of formula (IC):

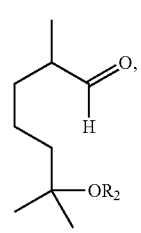
(IC)

adjusting the pH of the aqueous mixture to a first pH value that is between 6 and 10 to obtain a first organic phase that comprises the compound of formula (IC) and a first aqueous phase that comprises a salt of compound of formula (I);

separating the first aqueous phase from the first organic phase;

optionally adding an oxidant to the separated first aqueous phase;

adjusting the pH of the first aqueous solution to a second pH value that is not greater than about 5 to obtain a second organic phase that comprises the compound of formula (I) wherein $R_1$ is H and a second aqueous phase; and separating the second organic phase from the second aqueous phase to obtain the compound of formula (I) wherein $R_1$ is H.

In one embodiment, the aqueous mixture comprising the compound of formula (I) and the compound of formula (IC) is obtained by ozonolysis of a compound having the formula IB

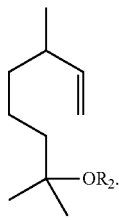

(IB)

The invention also relates to a compound of formula I, II, III, IV, V, VI, or VII below or a salt thereof:

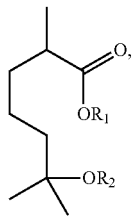

(I)

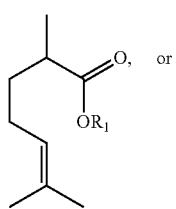

(II)

or

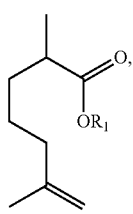

(III)

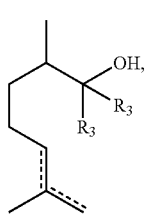

(IV)

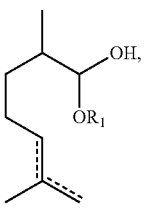

(V)

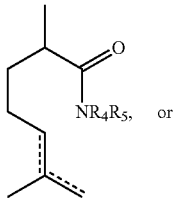

(VI)

or

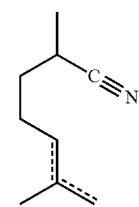

(VII)

wherein
one of the ---- is a single bond and the other is double bound, each of $R_1$, $R_4$, and $R_5$, independently, is H, unsubstituted or substituted $C_1$-$C_{10}$ alkyl, or unsubstituted or substituted $C_2$-$C_{10}$ alkenyl, $R_2$ is H, unsubstituted or substituted $C_1$-$C_{10}$ alkyl, or $COR_a$, in which $R_a$ is H or unsubstituted or substituted $C_1$-$C_{10}$ alkyl, and $R_3$ is unsubstituted or substituted $C_1$-$C_{10}$ alkyl.

In one embodiment, the salt of a compound of any of formulae described herein, is formed by reacting a —COOH group of the compound with a base to form an alkali metal salt such as $Na^+$, $K^+$, $Li^+$, an alkali earth metal salt such as $Mg^{2-}$ or $Ca^{2+}$, an organic amine salt, or an organic phosphonium salt.

The invention also relates to a compound of formula I, II III, IV, V, VI, or VII, or a salt thereof, generated by the methods described herein.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
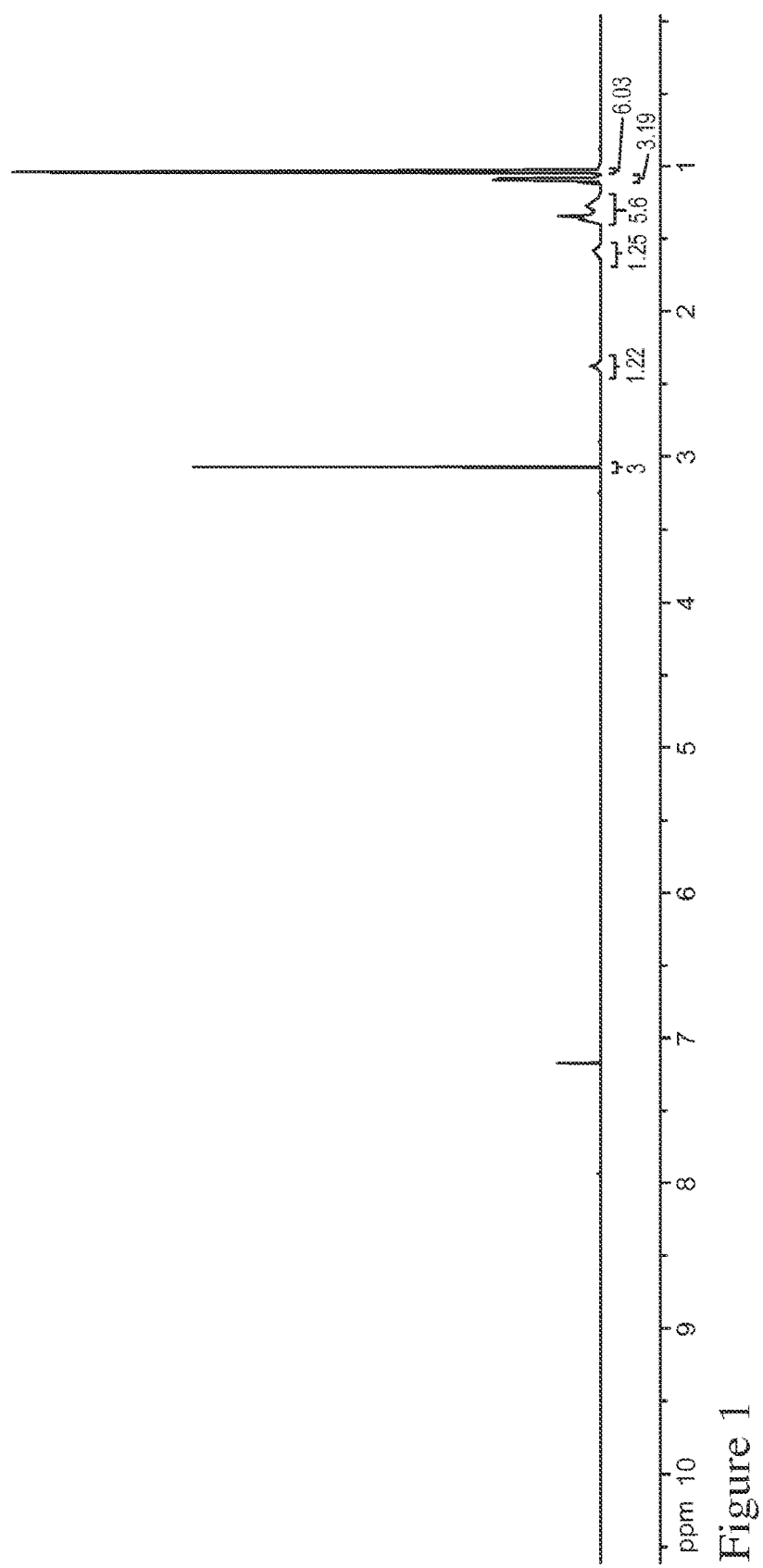
FIG. 1 is a $^1$H NMR spectrum of 6-methoxy-2,6-dimethylheptanoic acid.

Over-oxidation is observed in almost all ozonolysis procedures for generating aldehydes. The over-oxidized product, e.g., the corresponding acid, is generally regarded as waste and therefore negatively impacts the economics of aldehyde production. This invention relates to a cost-efficient isolation process of the acid product and use of the acid to offset or even reverse the negative impact mentioned above.

The invention relates to methods of producing acids and esters from terpenes or terpene analogs. In particular, this invention relates to ozonolysis of hydroxy- and alkoxy-citronellenes (e.g., 2,6-dimethyloct-7-en-2-ol and 7-methoxy-3,7-dimethyloct-1-ene) and producing an acid from either a reductive or oxidative ozonolysis procedure. This invention further relates to the derivatization of the acid to produce an ester, an unsaturated acid, or ester thereof. The compounds produced by the methods described herein can be used in, for example, flavors and fragrances due to their unique aroma properties.

In one aspect, the invention relates to a method of synthesizing a compound formula I or a salt thereof:

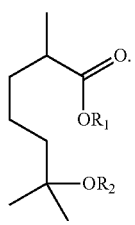
(I)

In this formula, $R_1$ is H, unsubstituted or substituted $C_1$-$C_{10}$ alkyl, or unsubstituted or substituted $C_2$-$C_{10}$ alkenyl, and $R_2$ is H, unsubstituted or substituted $C_1$-$C_{10}$ alkyl, or $COR_a$, in which $R_a$ is H or unsubstituted or substituted $C_1$-$C_{10}$ alkyl. The method includes reacting a compound having the formula IB

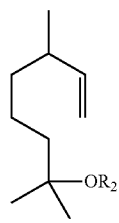
(IB)

with ozone and subsequently with an oxidant (i.e., an oxidizing agent) different from ozone to obtain the compound of formula (I) wherein $R_1$ is H Alternatively, the method includes
reacting a compound having the formula IB with ozone and subsequently with a reductant (i.e., a reducing agent) to obtain a mixture comprising the compound of formula (I) wherein $R_1$ is H and a compound of formula (IC):

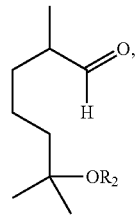
(IC)

and
separating the compound of formula (I) wherein $R_1$ is H from the compound of formula (IC).

In another aspect, the invention relates to a method of producing a compound of formula I or a salt thereof, the method including providing an aqueous mixture comprising the compound of formula (I) wherein $R_1$ is H and a compound of formula (IC):

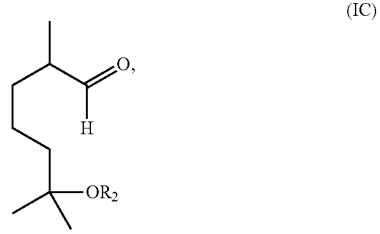
(IC)

adjusting the pH of the aqueous mixture to a first pH value that is between 6 and 10 to obtain a first organic phase that comprises the compound of formula (IC) and a first aqueous phase that comprises a salt of compound of formula (I);

separating the first aqueous phase from the first organic phase;

optionally adding an oxidant to the separated first aqueous phase;

adjusting the pH of the first aqueous solution to a second pH value that is not greater than about 5 to obtain a second organic phase that comprises the compound of formula (I) wherein $R_1$ is H and a second aqueous phase; and separating the second organic phase from the second aqueous phase to obtain the compound of formula (I) wherein $R_1$ is H.

In one embodiment, the aqueous mixture comprising the compound of formula (I) and the compound of formula (IC) is obtained by ozonolysis of a compound having the formula IB

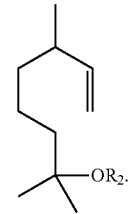
(IB)

In one embodiment, the reaction of the compound of formula IB with ozone or the ozonolysis of the compound of formula IB is carried out in the presence of a solvent. For example, the solvent comprises water, an organic solvent or a mixture there of. For example, the solvent comprises water and one or more organic solvents. For example, the organic solvent is an acid or alcohol or a mixture thereof. For example, the organic solvent is acetic acid, nonanoic acid, propanoic acid, palmitic acid, myristic acid, lauric acid, octanoic acid, methanol, isopropanol, ethanol, or a mixture thereof.

In one embodiment, the reaction of the compound of formula IB with ozone is carried out in the absence of a solvent such as water and an organic solvent.

In one embodiment, the mixture comprising the compound of formula (I) wherein $R_1$ is H and the compound of formula (IC) is an aqueous mixture.

In one embodiment, separating the compound of formula (I) from the compound of formula (IC) is performed by:

adjusting the pH of the aqueous mixture to a first pH value that is between 6 and 10 to obtain a first organic phase that comprises the compound of formula (IC) and a first aqueous phase that comprises a salt of compound of formula (I);

separating the first aqueous phase from the first organic phase;

optionally adding an oxidant to the separated first aqueous phase;

adjusting the pH of the first aqueous solution to a second pH value that is not greater than 5 (e.g., not greater than 4, such as a pH value between 0 and 4) to obtain a second organic phase that comprises the compound of formula (I) wherein $R_1$ is H and a second aqueous phase; and separating the second organic phase from the second aqueous phase to obtain the compound of formula (I) wherein $R_1$ is H.

In one embodiment, an oxidant (e.g., a peroxide) is added to the first aqueous phase before the pH is adjusted to not greater than 5 (e.g., not greater than 4, such as a pH value between 0 and 4).

In one embodiment, the method further includes reacting the compound of formula I wherein $R_1$ is H, with an alcohol $R_bOH$ wherein $R_b$ is unsubstituted or substituted $C_1$-$C_{10}$ alkyl or unsubstituted or substituted $C_2$-$C_{10}$ alkenyl, to produce a compound of formula I wherein $R_1$ is unsubstituted or substituted $C_1$-$C_{10}$ alkyl, or unsubstituted or substituted $C_2$-$C_{10}$ alkenyl.

In one embodiment, the method further includes performing an elimination reaction on the compound of formula I to obtain a compound of formula II or III or a mixture thereof:

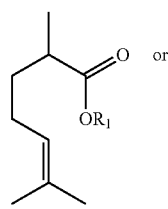

(II)

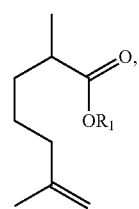

(III)

wherein $R_1$ is H, unsubstituted or substituted $C_1$-$C_{10}$ alkyl, or unsubstituted or substituted $C_2$-$C_{10}$ alkenyl. For example, the elimination reaction is performed in a solvent comprising an alcohol (e.g., methanol, ethanol, isopropanol, butanol and the like) and an acid (e.g., p-toluenesulfonic acid or tosic acid) at, e.g., room temperature.

In one embodiment, the oxidant used in the method is a peroxide (e.g., hydrogen peroxide).

In one embodiment, the reductant used in the method is a reducing agent suitable for producing an aldehyde in a reductive ozonolysis process. For example, the reductant is $H_2$ in the presence or absence of a suitable catalyst, such as Pd, Ni, Rh, Pt, or Ru. For example, the reductant is sodium bisulfite ($NaHSO_3$). For example, the reductant is triphenylphosphine, thiourea, zinc dust, or dimethyl sulfide.

An example of the methods of the invention is illustrated as in Scheme 1 below ($R_1$ and $R_2$ in Schemes 1 and 2 are as defined herein for formula I unless otherwise specified).

Scheme 1

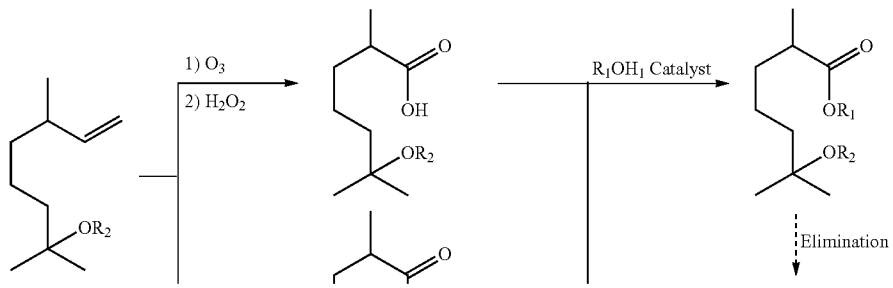

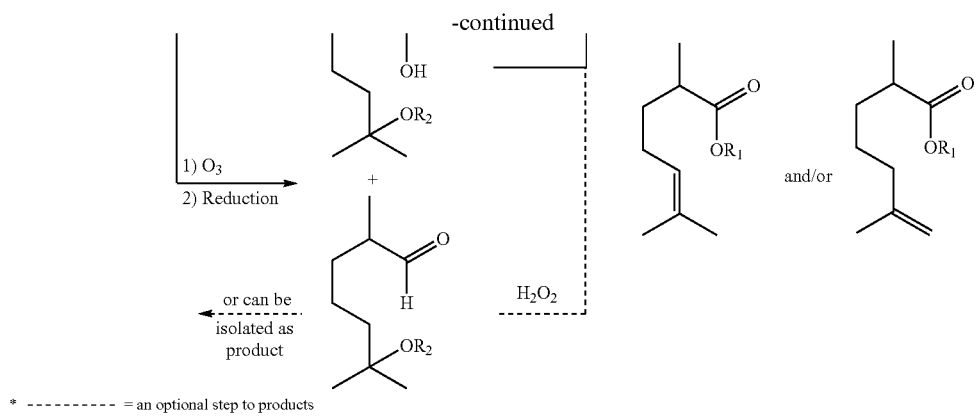

In Scheme 1 above, the terpene-derived acid or ester product can be formed via either oxidative (top route) or reductive (bottom route) ozonolysis of methoxycitronellene, hydroxycitronellene, acetoxycitronellene, or alkoxycitronellene. When the acid and the corresponding aldehyde are formed in the reductive ozonolysis procedure (bottom route), the acid can be separated from the aldehydic product by bringing the pH to between 6 and 10 (e.g., between 7 and 10) to form the salts of the terpene-derived acids (see, e.g., Scheme 2 below).

the resultant reaction mixture is quite low (e.g., about 1-3). An alkaline compound (e.g., $NaHCO_3$, $Na_2CO_3$, NaOH, $K_2CO_3$, KOH, and/or dibasic phosphate, or other inexpensive base) can be added to adjust the pH value to between 6 and 10. Following this pH adjustment step, the reaction mixture is phase separated in the presence of water to give an organic phase comprising the aldehyde, and an aqueous phase comprising the salt of the acid, as illustrated in Scheme 2, above. Following phase separation, hydrogen peroxide, or any other suitable oxidant, can be added to the

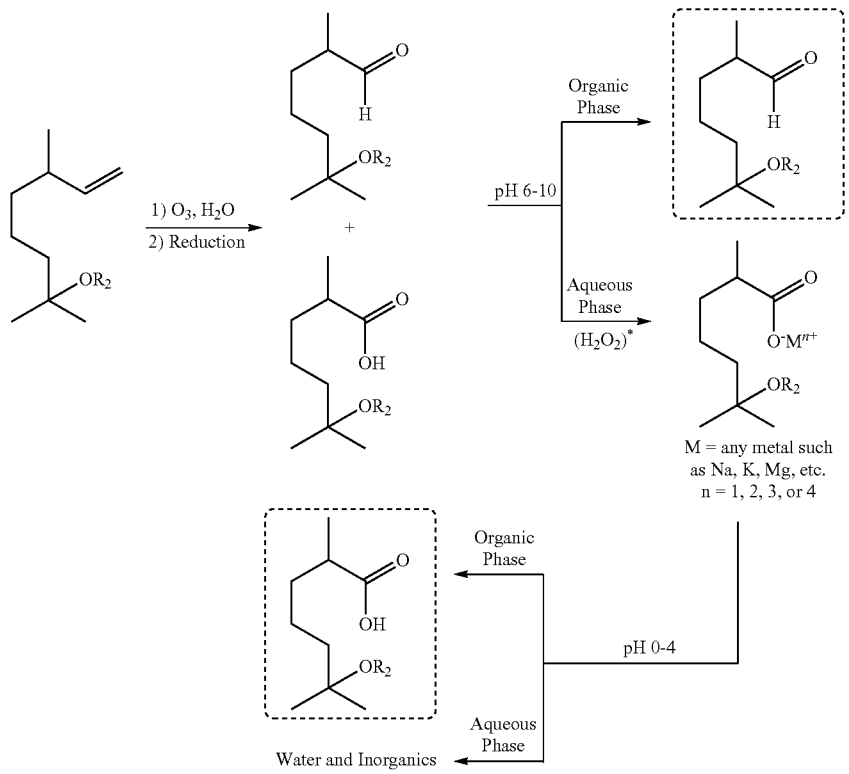

* $H_2O_2$ or other oxidant is optionally dded to the basic aqueous mixture and stirred to convert any trace aldehyde present into acid/acid salt.

In one embodiment, the reductive ozonolysis is performed in an aqueous mixture without a buffer, and the pH value of aqueous phase to convert any trace aldehyde present in the aqueous phase into the corresponding acid and/or acid salt.

Once the acid salt product has been isolated in the aqueous phase, the pH value of the aqueous phase can be adjusted such that the target acid is formed and phase separated from the aqueous phase. Additional organic extraction can be performed if needed to obtain additional amount of the target acid.

As illustrated in Scheme 1 above, the acids obtained can then be esterified to generate esters. Additionally, these esters can undergo subsequent or tandem elimination reaction in the presence of an acid to generate ester-olefins, such as compounds of formulae II and III.

In one embodiment, methoxycitronellene (i.e., 7-methoxy-3,7-dimethyloct-1-ene) is combined with water and cooled to, e.g., about 10° C. while stirring rapidly in, e.g., a jacketed glass reactor equipped with overhead stirrer and controlled gas diffusion. Ozone (e.g., 5-7% by weight in oxygen) is then diffused into the mixture until all of the starting material is consumed and the reaction temperature is maintained at, e.g., below about 22° C. The reaction vessel is then purged with $N_2$ and the mixture is transferred into a high-pressure reactor and charged with palladium black (e.g., 0.2% by weight). The reaction mixture is then stirred under hydrogen atmosphere (e.g., 300 psi) at e.g., about 75° C. for e.g., about 2.5 hours until the peroxide value of the reaction mixture approaches zero. The mixture is then filtered to remove the catalyst and placed in a separatory funnel. The organic phase is separated and washed with deionized water to afford a solution containing methoxymelonal and its corresponding acid, i.e., 6-methoxy-2,6-dimethylheptanoic acid. Next, the organic phase is further extracted with a basic aqueous solution, e.g., 10% (aq.) $Na_2CO_3$, to separate any residual acid byproduct from the aldehyde. The aqueous phase is charged with a peroxide (e.g., hydrogen peroxide). Next, an acid, e.g., $NaHSO_3$, is added to the reaction mixture until no excess peroxide can be measured with KI starch strips. The aqueous mixture is then acidified to a pH~2-3 by e.g., adding 6N (aq.) HCl. Following the pH adjustment, an organic phase is obtained, which contains 6-methoxy-2,6-dimethylheptanoic acid. The acidic aqueous phase can be further extracted using, e.g., EtOAc to obtain an additional amount of the desired acid product after evaporation.

In one embodiment, 6-methoxy-2,6-dimethylheptanoic acid is dissolved in methanol and an acid, e.g., conc. $H_2SO_4$, is added to the stirring reaction mixture. The mixture is stirred at room temperature overnight, then heated to e.g., about 50° C. for about 2 hours, and refluxed for an additional 3 hours. The solvent is removed via evaporation and the resulting crude residue is dissolved in EtOAc. The organic solution is washed with e.g., 10% (aq.) $Na_2CO_3$ and then evaporated to afford methyl 6-methoxy-2,6-dimethylheptanoate.

In one embodiment, 6-methoxy-2,6-dimethylheptanoic acid is dissolved in EtOH and charged with an acid, e.g., Tosic Acid. The reaction mixture is stirred at e.g., room temperature for 3 days until all the starting material is consumed. The reaction mixture is concentrated in the presence of silica gel to obtain a mixture of ethyl 2,6-dimethylhept-5-enoate and ethyl 2,6-dimethylhept-6-enoate.

In one embodiment, the acid or ester product from the method of the invention can be >80% pure (e.g., >90%, >95%, >98%, or >99% pure). $^1$H NMR and gas chromatography can be used to characterize the desired acid or ester product. For example, the acid or ester product is free of aldehydic material or starting material. For example, the impurities (e.g., the starting material terpenes such as methoxycitronellene, hydroxycitronellene, acetoxycitronellene, and alkoxycitronellenes, or aldehydic product such as methoxymelonal) in the acid or ester product is less than 20% (e.g., <10%, <5%, <2%, or <1%).

The invention also relates to a process of separation of an acid and an aldehyde following a reductive ozonolysis of an olefin (e.g., a terpene). A representative process scheme is shown in Scheme 2 above.

In one embodiment, the ozone used in the ozonolysis is generated by electrolyzing water.

In some embodiments, the methods described herein further include derivatizing the compound of formula II or III described herein, such as reduction, conversion to an amide, a nitrile (e.g., via the dehydration of an amide with $SOCl_2$ or $P_2O_5$), or conversion to a tertiary alcohol through alkyl addition. In one embodiment, the compounds of formula II or III described herein are converted to an alcohol of formula IV via a reaction depicted in Scheme 3 below.

Scheme 3

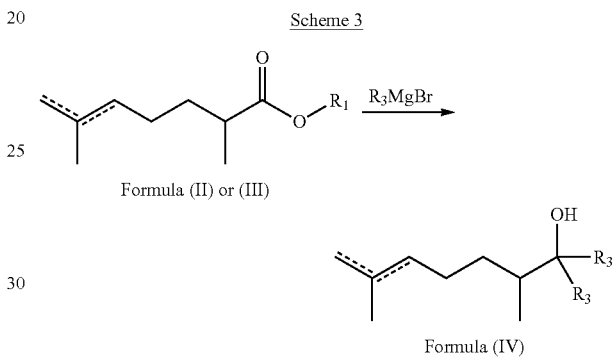

Formula (II) or (III)

Formula (IV)

In Scheme 3 above, one of the ---- is a single bond and the other is double bound, $R_1$ and $R_2$ are as defined herein for formula I unless otherwise specified, and $R_3$ is unsubstituted or substituted $C_1$-$C_{10}$ alkyl, e.g., methyl or ethyl. In one embodiment, under an inert gas, e.g., nitrogen, a solution of $R_3MgBr$, e.g., methylmagnesium bromide (e.g., in THF) is added (e.g., slowly) into a solution of a compound of formula II or III, e.g., sec-butyl 2,6-dimethylhept-5-enoate (e.g., in THF) at a first temperature, e.g., 0° C., for e.g., about 30 minutes. After stirring for e.g., 30 minutes at 0° C., the reaction mixture is stirred at a temperature greater than the first temperature, e.g., room temperature for, e.g., another 14 hours, or until all the starting material is consumed. The reaction mixture is then cooled down to, e.g., 0° C. and quenched, e.g., with saturated $NH_4Cl$ in $H_2O$. All organic solvent (e.g., THF) is then removed, e.g., by evaporation. Next, an acid, e.g., acetic acid (e.g., 15% in water) is added to the residue. The aqueous layer is then extracted with an organic solvent, e.g., ethyl acetate and the organic fractions containing the product, a compound of formula IV, are combined. The compound of formula IV, e.g., 2,3,7-trimethyloct-6-en-2-ol, 2,3,7-trimethyloct-7-en-2-ol, or a mixture thereof, is then purified by, e.g., removal of the solvent and column chromatography (e.g., Silica gel, EtOAc/heptane: 5-10%).

In some embodiments, the product of the method of the invention has an overall yield of no less than 60%, e.g., no less than 70%, no less than 80%, or no less than 90%.

In some embodiments, the product of the method of the invention contains more than 80% of compound of formula I. In some embodiments, the product of the method of the invention contains more than 85%, 90%, 92%, 95%, 97%, 98%, 98.5%, or 99% of compound of formula I. For example, the product is free of undesired byproduct or starting material. For example, the impurities (e.g., undesired byproduct or starting material such as methoxycitronellene, hydroxycitronellene, acetoxycitronellene, and alkoxycitronellenes) in the acid or ester product is less than 20% (e.g., <15%, <10%, <8%, <5%, <3%, <2%, <1.5%, or <1%).

In some embodiments, the product of the method of the invention contains more than 80% of compound of formula II and/or III. In some embodiments, the product of the method of the invention contains more than 85%, 90%, 92%, 95%, 97%, 98%, 98.5%, or 99% of compound of formula II and/or III. For example, the product is free of undesired byproduct or starting material. For example, the impurities (e.g., undesired byproduct or starting material such as methoxycitronellene, hydroxycitronellene, acetoxycitronellene, and alkoxycitronellenes) in the acid/ester-olefin product is less than 20% (e.g., <15%, <10%, <8%, <5%, <3%, <2%, <1.5%, or <1%).

In some embodiments, the product of the method of the invention contains more than 80% of compound of formula IV. In some embodiments, the product of the method of the invention contains more than 85%, 90%, 92%, 95%, 97%, 98%, 98.5%, or 99% of compound of formula IV. For example, the product is free of undesired byproduct or starting material. For example, the impurities (e.g., undesired byproduct or ester-olefin starting material such as sec-butyl 2,6-dimethylhept-5-enoate) in the product is less than 20% (e.g., <15%, <10%, <8%, <5%, <3%, <2%, <1.5%, or <1%).

It will be appreciated that the methods disclosed herein are suitable for both large-scale and small-scale preparations of the desired compounds. In preferred embodiments of the methods described herein, the compounds of formula I (or compounds of formula II, III, IV, V, VI, or VII) may be prepared on a large scale, for example on an industrial production scale rather than on an experimental/laboratory scale. For example, the methods of the disclosure allow the preparation of batches of at least 1 g, or at least 5 g, or at least 10 g, or at least 100 g, or at least 1 kg, or at least 10 kg, or at least 100 kg of product.

The invention also relates to a compound of formula I, II, III, IV, V, VI, or VII below or a salt thereof:

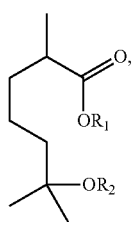
(I)

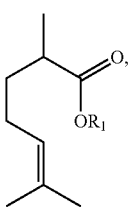
(II)

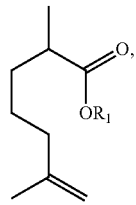
(III)

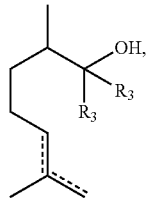
(IV)

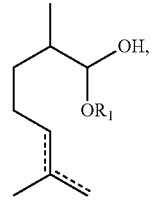
(V)

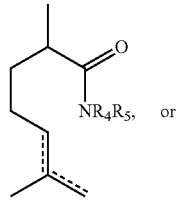
(VI)

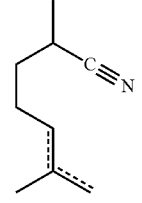
(VII)

wherein
one of the ---- is a single bond and the other is double bound, each of $R_1$, $R_4$, and $R_5$, independently, is H, unsubstituted or substituted $C_1$-$C_{10}$ alkyl, or unsubstituted or substituted $C_2$-$C_{10}$ alkenyl, $R_2$ is H, unsubstituted or substituted $C_1$-$C_{10}$ alkyl, or $COR_a$, in which $R_a$ is H or unsubstituted or substituted $C_1$-$C_{10}$ alkyl, and $R_3$ is unsubstituted or substituted $C_1$-$C_{10}$ alkyl.

For example, $R_1$ is substituted or unsubstituted alkyl having 1, 2, 3, 4, 5, 6, 7, 8, 9, or 10 carbon atoms, $R_1$ is substituted or unsubstituted alkenyl having 2, 3, 4, 5, 6, 7, 8, 9, or 10 carbon atoms and one, two, or three carbon-carbon double bonds.

For example, $R_2$ is H or substituted or unsubstituted alkyl having 1, 2, 3, 4, 5, 6, 7, 8, 9, or 10 carbon atoms.

For example, $R_2$ is $COR_a$, in which $R_a$ is H or unsubstituted or substituted alkyl having 1, 2, 3, 4, 5, 6, 7, 8, 9, or 10 carbon atoms.

For example, in formula I, II, III, or V, $R_1$ is unsubstituted $C_1$-$C_3$ alkyl (e.g., alkyl having 1, 2, or 3 carbon atoms) or unsubstituted $C_2$-$C_3$ alkenyl (e.g., alkenyl having 2 or 3 carbon atoms such as allyl).

For example, in formula I, II, III, or V, $R_1$ is unsubstituted $C_3$-$C_9$ alkyl (e.g., alkyl having 3, 4, 5, 6, 7, 8, or 9 carbon atoms).

For example, in formula I, $R_2$ is unsubstituted $C_1$-$C_3$ alkyl (e.g., alkyl having 1, 2, or 3 carbon atoms) or $COCH_3$.

For example, in formula I, $R_2$ is unsubstituted $C_3$-$C_9$ alkyl (e.g., alkyl having 3, 4, 5, 6, 7, 8, or 9 carbon atoms).

For example, the compounds of formula I, II, or III, include

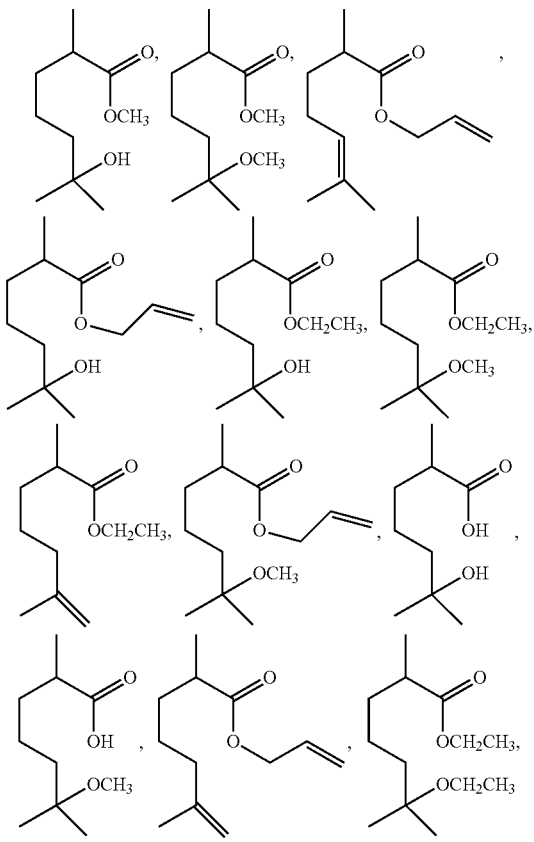

and salts thereof.

For example, in formula IV, $R_3$ is substituted or unsubstituted alkyl having 1, 2, 3, 4, 5, 6, 7, 8, 9, or 10 carbon atoms, e.g., unsubstituted $C_1$-$C_3$ alkyl (e.g., alkyl having 1, 2, or 3 carbon atoms). For example, the compound of formula IV includes 2,3,7-trimethyloct-6-en-2-ol and 2,3,7-trimethyloct-7-en-2-ol.

For example, in formula VI, each of $R_4$ and $R_5$ is independently, H, substituted or unsubstituted alkyl having 1, 2, 3, 4, 5, 6, 7, 8, 9, or 10 carbon atoms, or substituted or unsubstituted alkenyl having 2, 3, 4, 5, 6, 7, 8, 9, or 10 carbon atoms and one, two, or three carbon-carbon double bonds. For example, each of $R_4$ and $R_5$ is independently, H or unsubstituted alkyl having 1, 2, 3, 4, 5, 6, 7, 8, 9, or 10 carbon atoms.

The details of one or more embodiments of the invention are set forth in the accompanying description below. Unless defined otherwise, all technical and scientific terms used herein have the same meaning as commonly understood by one of ordinary skill in the art to which this invention belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116). In some formulae of the present application, one or more chiral centers are identified by an asterisk placed next to the chiral carbon. In other formulae, no chiral center is identified, but the chiral isomers are nonetheless covered by these formulae.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Some compounds of the present invention can exist in a tautomeric form which is also intended to be encompassed within the scope of the present invention. "Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts, or organic phosphonium salts.

The term "alkyl" as used herein refers to a branched or unbranched saturated hydrocarbon group typically although not necessarily containing 1 to about 10 carbon atoms, such as methyl, ethyl, n-propyl, isopropyl, n-butyl, isobutyl, t-butyl, octyl, and the like.

The term "alkenyl" as used herein refers to a branched or unbranched unsaturated hydrocarbon group typically although not necessarily containing 2 to about 10 carbon atoms and 1-8 carbon-carbon double bonds, such as ethylene, n-propylene, isopropylene, n-butylene, isobutylene, t-butylene, octylene, and the like.

By "substituted" as in "substituted alkyl," "substituted alkenyl," and the like, it is meant that in the alkyl, alkenyl, or other moiety, at least one hydrogen atom bound to a carbon atom is replaced with one or more non-hydrogen substituents, e.g., by a functional group.

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$)$_5$ carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano isocyano (—N cyanato isocyanato (—O—N$^+$≡C$^-$), isothiocyanato (—S—C≡N), azido (—N═N$^+$═N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR═NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR═N(alkyl), where R=hydrogen, alkyl, aryl, alkaryl, etc.), arylimino (—CR═N(aryl), where R=hydrogenhydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O)$_2$), phosphinato (—P(O)(O)), phospho (—PO$_2$), phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention.

All percentages and ratios used herein, unless otherwise indicated, are by weight.

EXAMPLES

Example 1: 6-Methoxy-2,6-Dimethylheptanoic Acid and Esters

Acid Isolation

Methoxycitronellene (i.e., 7-methoxy-3,7-dimethyloct-1-ene, 350 g, 0.486 mol) was combined with water (700 g) and cooled to 10° C. while stirring rapidly in a jacketed glass reactor equipped with overhead stirrer and controlled gas diffusion. 5-7% by weight ozone in oxygen was diffused into the reaction mixture at a flow rate of 10 L/min over 110 minutes until all of the starting material was consumed, while maintaining a reaction temperature below 22° C. The reaction vessel was then purged with N$_2$ and the mixture was transferred into a high-pressure reactor and charged with palladium black (0.2% by weight). The reaction mixture was stirred under hydrogen atmosphere (300 psi) at 75° C. for 2.5 hours until the peroxide value of the reaction mixture approached zero. The mixture was then filtered to remove the catalyst and placed in a separatory funnel. The organic phase was separated and washed with deionized water (150 mL) to afford a solution containing a crude material consisting predominantly of methoxymelonal and its corresponding acid, i.e., 6-methoxy-2,6-dimethylheptanoic acid (336 g).

The organic phase was further extracted with 10% (aq.) Na$_2$CO$_3$ to remove any residual acid byproduct. The phases were separated and the organic phase contained clean methoxymelonal (275 g). The aqueous phase was charged with hydrogen peroxide (2.4 g, 30 wt. %) and stirred at room temperature overnight. The next day, NaHSO$_3$ was added to the reaction mixture until no excess peroxide could be measured with KI starch strips. The aqueous mixture was acidified to a pH~2-3 with the slow addition of 6N (aq.) HCl. Following the pH adjustment, an organic phase separated out, which contained almost exclusively the corresponding terpene-derived acid, 6-methoxy-2,6-dimethylheptanoic acid (45.1 g). $^1$H NMR for this material can be seen in FIG. 1. The acidic aqueous phase was extracted again using EtOAc to obtain an additional amount (4.5 g) of the desired acid product after evaporation.

Figure 2:
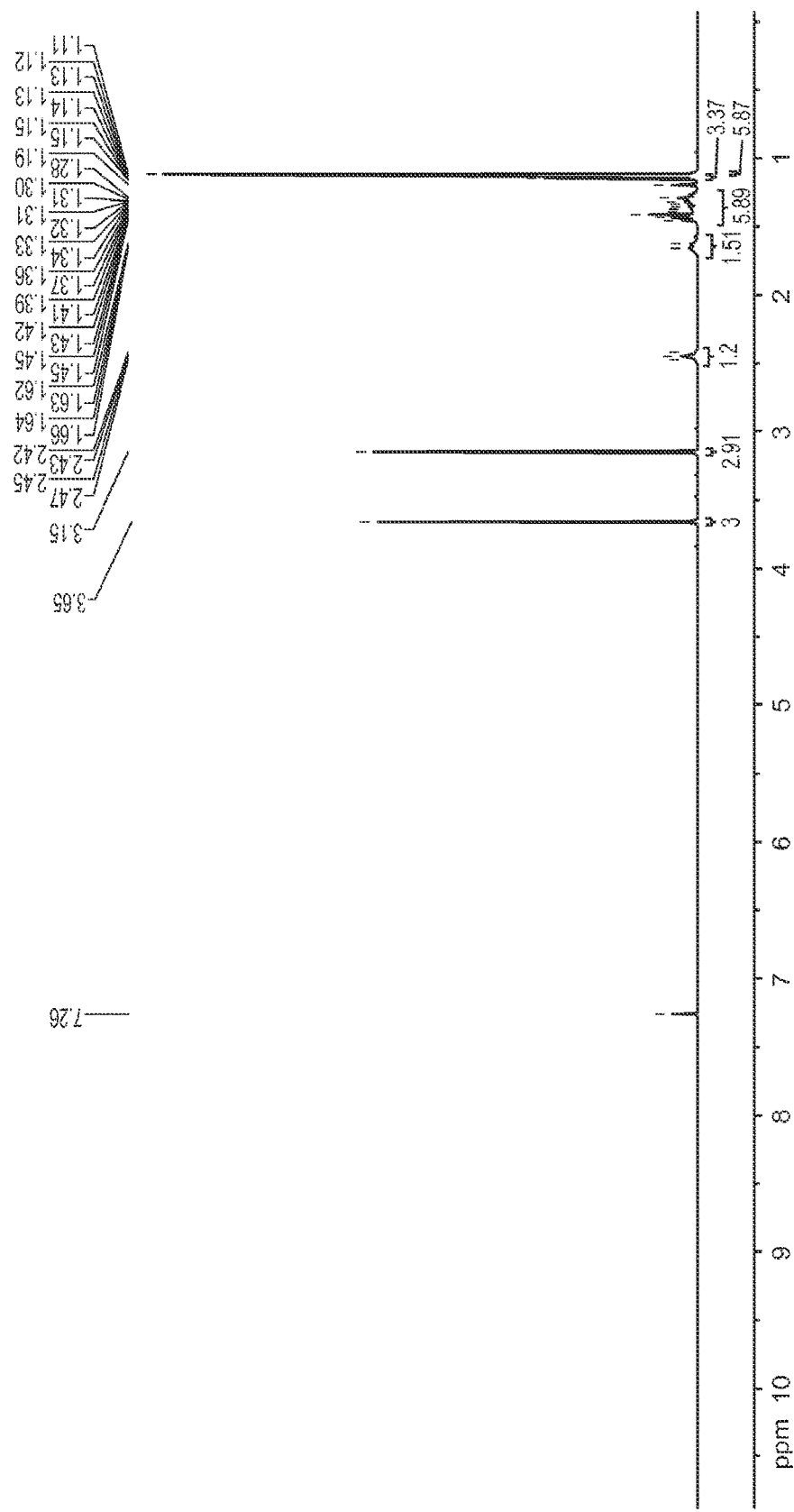
FIG. 2 is a $^1$H NMR spectrum of methyl 6-methoxy-2,6-dimethylheptanoate.

Esterification 6-methoxy-2,6-dimethylheptanoic acid (1.7 g, 0.9 mmol) was dissolved in MeOH (10 mL) and 2 drops of conc. $H_2SO_4$ were added to the stirring reaction mixture. The mixture was stirred at room temperature overnight, then heated to 50° C. for 2 hours, and refluxed for an additional 3 hours. The solvent was removed via evaporation and the resulting crude residue was dissolved in EtOAc (50 mL). The organic solution was washed with 10% (aq.) $Na_2CO_3$ (50 ml of 10% by weight in water) and then evaporated to afford the methyl ester, i.e., methyl 6-methoxy-2,6-dimethylheptanoate (1.6 g). $^1$H NMR of this material is shown in FIG. 2.

Figure 3:
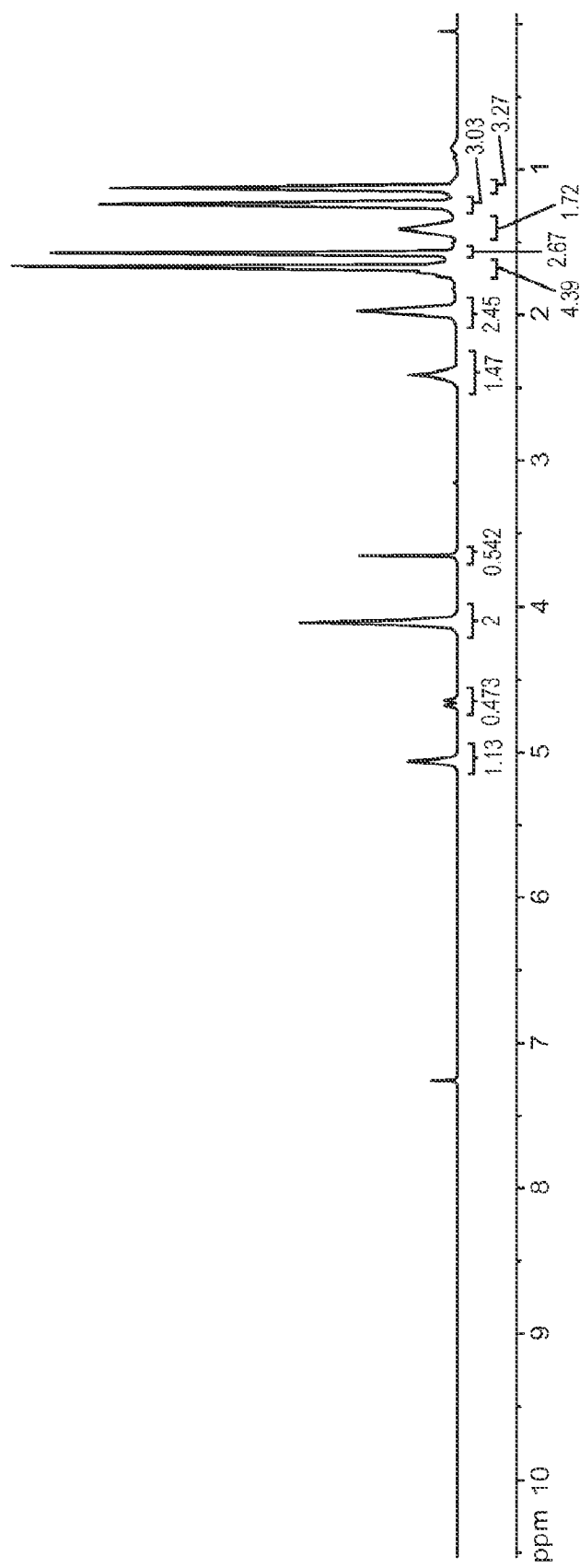
FIG. 3 is a $^1$H NMR spectrum of a mixture of ethyl 2,6-dimethylhept-5-enoate and ethyl 2,6-dimethylhept-6-enoate.

Esterification and Elimination 6-methoxy-2,6-dimethylheptanoic acid (4.0 g) was dissolved in EtOH (20 mL) and charged with Tosic Acid (400 mg). The reaction mixture was stirred at room temperature for 3 days until all the starting material was consumed. The reaction mixture was concentrated in the presence of silica gel, which was used in silica gel chromatography (2-5% gradient of EtOAc in Heptane) to obtain a mixture of ethyl 2,6-dimethylhept-5-enoate and ethyl 2,6-dimethylhept-6-enoate (1.5 g). $^1$H NMR of the product is shown in FIG. 3 (note the presence of the methyl ester in the mixture, likely due to methanol present in the EtOH as an EtOH denaturant).

Example 2: Additional Analogs

6-Hydroxy-2,6-dimethylheptanoic acid was prepared in a fashion similar to that described in Example 1, using hydroxycitronellene (i.e., 2,6-dimethyloct-7-en-2-ol) as a starting material. Several ester derivatives of 6-hydroxy-2,6-dimethylheptanoic acid were also prepared in a fashion similar to that described in Example 1.

Example 3: Derivatives of Terpene Esters

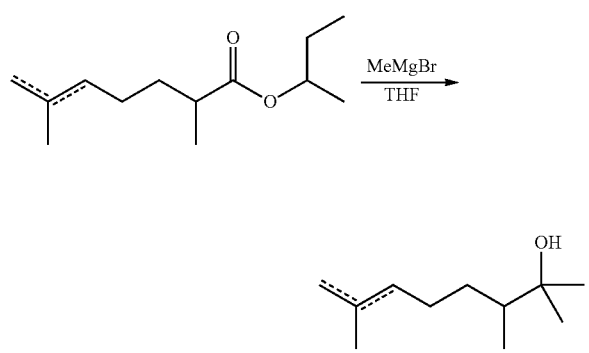

* one of the ---- is a single bond and the other is double bound,

Under nitrogen, 54.4 mL of methylmagnesium bromide solution (3 M in THF from Sigma-Aldrich) was added slowly into sec-butyl 2,6-dimethylhept-5-enoate (14.0 g, 0.65 mol) in THF (800 mL) at 0° C. over 30 minutes. After stirring for 30 minutes at 0° C., the cooling bath was removed and the reaction mixture was stirred for another 14 hours at room temperature. TLC showed that all starting material was consumed. The reaction mixture was cooled down to 0° C. and quenched with saturated $NH_4Cl$ in $H_2O$. All of the organic solvent (THF) was then evaporated and 50 mL acetic acid (15% in water) was added to the residue. The aqueous layer was then extracted 2× with ethyl acetate (200 mL then 100 mL) and the organic fractions were combined. Evaporation of the solvent gave crude product. 8.3 g of clean product was obtained through column chromatography (Silica gel, EtOAc/heptane: 5-10%). The clean product was a mixture of 2,3,7-trimethyloct-6-en-2-ol and 2,3,7-trimethyloct-7-en-2-ol with a molar ratio of 5.45 to 1.

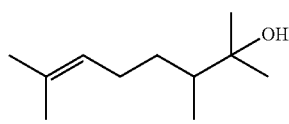

2,3,7-trimethyloct-6-en-2-ol

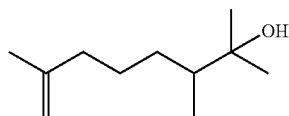

Figure 4:
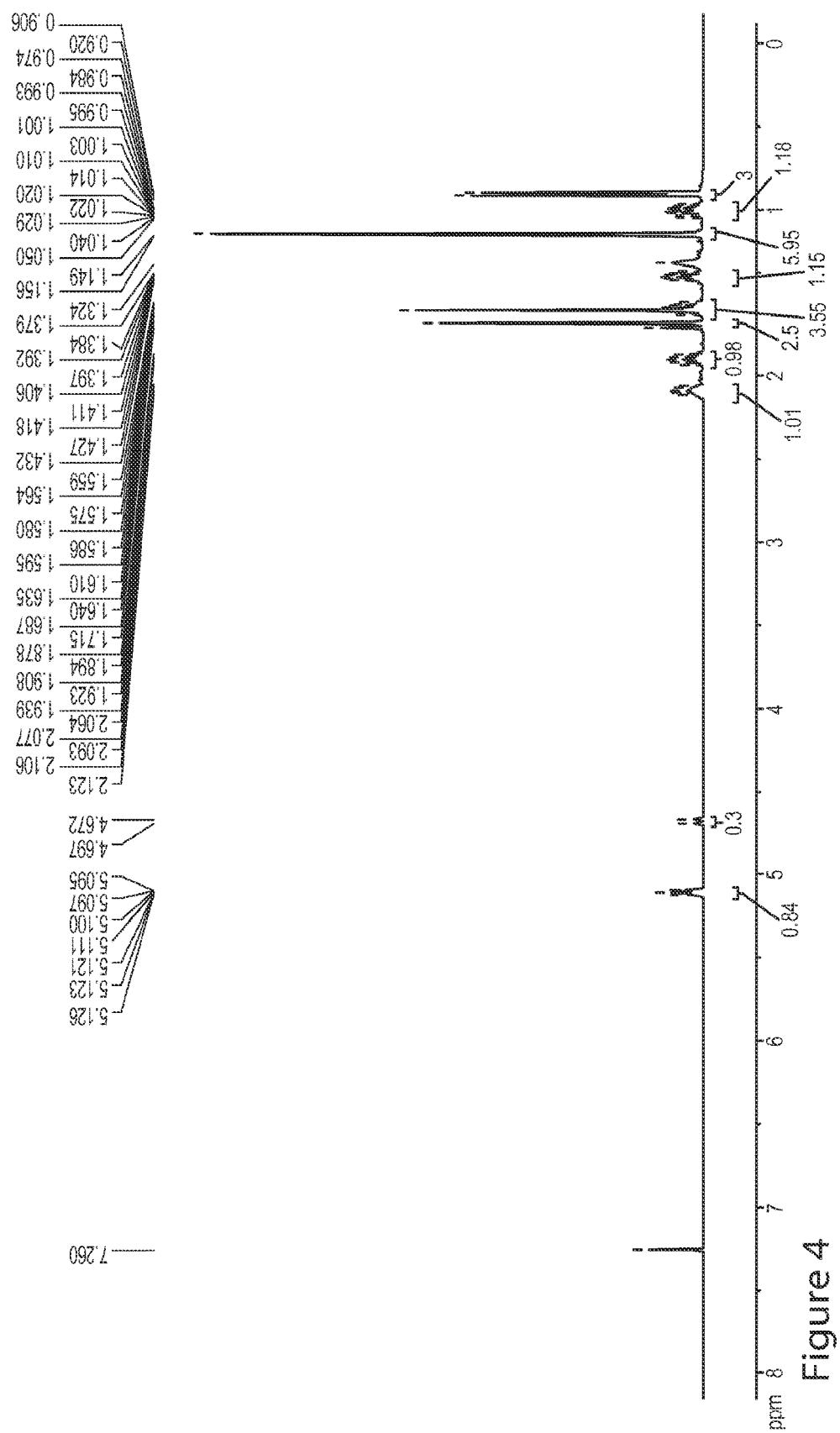
FIG. 4 is a $^1$H NMR spectrum of a mixture of 2,3,7-trimethyloct-6-en-2-ol and 2,3,7-trimethyloct-7-en-2-ol.

2,3,7-trimethyloct-7-en-2-ol $^1$H NMR (CDCl$_3$, 500 MHz) of 2,3,7-trimethyloct-6-en-2-ol: δ 0.91 (d, J=7.0 Hz, 3H, —CH$_3$), 0.97-1.05 (m, 1H, —CH$_2$—), 1.15 (s, 3H, —CH$_3$), 1.16 (s, 3H, —CH$_3$), 1.38-1.43 (m, 1H, —CH$_2$—), 1.56-1.64 (m, 1H, —CH$_2$—), 1.61 (s, 3H, —CH$_3$), 1.69 (s, 3H, —CH$_3$), 1.88-1.94 (s, 1H, —CH$_2$—), 1.06-2.12 (s, 1H, —CH$_2$—), 5.10-5.13 (s, 1H, —CH=). FIG. 4 shows $^1$H NMR of a mixture of 2,3,7-trimethyloct-6-en-2-ol and 2,3,7-trimethyloct-7-en-2-ol.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:
1. A compound of Formula IV:

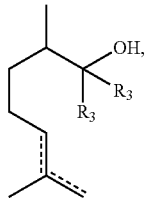

(IV)

or a salt thereof, wherein one of the ---- is a single bond and the other is double bound, and $R_3$ is unsubslituted or substituted $C_1$-$C_{10}$ alkyl,
wherein the compound is selected from 2,3,7-trimethyloct-6-en-2-ol, 2,3,7- trimethyloct-7-en-2-ol, and salts thereof.

2. A composition comprising 2,3,7-trimethyloct-6-en-2-ol, or 2,3,7-trimethyloct 7-en-2-ol, or salts thereof, or a mixture thereof.

3. A method of producing at least one compound according to claim 1, the method comprising:
providing an aqueous mixture of compound of Formula II or Formula III

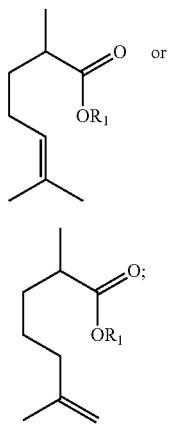

reacting the aqueous mixture with $R_3MgBr$, wherein $R_1$ is H, unsubstituted or substituted $C_1$-$C_{10}$ alkyl, or unsubstituted or substituted $C_2$-$C_{10}$ alkenyl, to form the compound of Formula IV.

4. The method of claim 3, wherein the reaction is performed under an inert gas.

5. The method of claim 4, wherein the $R_3MgBr$ in the presence of an organic solvent and is added to the aqueous mixture to form a reaction mixture which is then stirred at a first temperature for a first time period to produce an intermediate mixture.

6. The method of claim 5, the method further comprising stirring the intermediate mixture at a second temperature for a second time period to produce a final mixture.

7. The method of claim 6, the method further comprising cooling the final mixture and quenching the cooled final mixture to produce a quenched final mixture.

8. The method of claim 7, the method further comprising removing the organic solvent from the quenched final mixture to produce a residue.

9. The method of claim 8, the method further comprising adding an acid to the residue to form an aqueous layer.

10. The method of claim 9, the method further comprising extracting the aqueous layer with an organic solvent to obtain at least one organic fraction containing at least one compound of formula IV.

11. The method of claim 10, the method further comprising purifying the organic fraction.

12. The method of claim 11, wherein $R_1$ is $(CH)(CH_2)(CH_3)_2$ and $R_3$ is $CH_3$.

13. The method of claim 12, wherein the at least one compound of formula IV comprises 2,3,7-trimethyloct-6-en-2-ol, 2,3,7-trimethyloct-7-en-2-ol, or salts thereof, or a mixture thereof.

14. The composition of claim 2, wherein the composition comprises 2,3,7-trimethyloct-6-en-2-ol and 2,3,7-trimethyloct-7-en-2-ol, or salts thereof.

15. The composition of claim 14, wherein the composition comprises 2,3,7-trimethyloct-6-en-2-ol and 2,3,7-trimethyloct-7-en-2-ol, or salts thereof, in a ratio of about 5:5:1.

16. The composition of claim 2 wherein the composition is a fragrance composition.

17. The composition of claim 15, wherein the composition is a fragrance composition.

18. The composition of claim 14, wherein the composition comprises the mixture of 2,3,7-trimethyloct-6-en-2-ol and 2,3,7-trimethyloct-7-en-2-ol, having the proton NMR spectrum shown in FIG. 4.

19. The composition of claim 18, wherein the composition is a fragrance composition.

* * * * *

UNITED STATES PATENT AND TRADEMARK OFFICE
CERTIFICATE OF CORRECTION

PATENT NO. : 10,071,941 B2
APPLICATION NO. : 15/317642
DATED : September 11, 2018
INVENTOR(S) : Foley et al.

Page 1 of 1

It is certified that error appears in the above-identified patent and that said Letters Patent is hereby corrected as shown below:

In the Claims

In Claim 1, at Column 21, Line 15, "a salt (hereof" should be replaced with --a salt thereof--.

In Claim 1, at Column 21, Line 19, "2,3,7-trimcthyloct-7-en-2-ol" should be replaced with --2,3,7-trimethyloct-7-en-2-ol--.

In Claim 1, at Column 21, Line 16, "unsubslitutcd" should be replaced with --unsubstituted--.

In Claim 3, at Column 21, Line 47, the word --and-- should be inserted before the phrase "reacting the aqueous mixture".

Signed and Sealed this
Twentieth Day of November, 2018

Andrei Iancu
*Director of the United States Patent and Trademark Office*